United States Patent [19]

Becker et al.

[11] Patent Number: 5,079,345
[45] Date of Patent: Jan. 7, 1992

[54] PROTEINS HAVING GROWTH HORMONE ANABOLIC PROPERTIES WITH REDUCED EFFECT ON CAROHYDRATE METABOLISM

[75] Inventors: Gerald W. Becker; Carl J. Shaar, both of Indianapolis, Ind.

[73] Assignee: Eli Lilly and Company, Indianapolis, Ind.

[21] Appl. No.: 233,772

[22] Filed: Aug. 19, 1988

[51] Int. Cl.$^5$ .......................... C07K 13/00; C07K 7/10
[52] U.S. Cl. .................................... 530/399; 530/350; 530/324; 530/402
[58] Field of Search ................ 530/399, 350, 324, 402

[56] References Cited

PUBLICATIONS

Lewis et al., *Rec. Progr. Horm. Res.* 36, 477–508 (1980).
Li et al., *Mol. Pharmacol* 1, 47–52 (1965).
Graf et al., *J. Biol. Chem.* 257, 2365–2369 (1982).
Mills et al., *Endocrinology* 102, 1366–1376 (1978).
Reagan et al., *Endocrinology* 102, 1377–1386 (1978).
Reagan, C. R. et al., *Diabetes* 27, 883–888 (1978).
Mills et al., *Endocrinology* 107, 391–399 (1980).
Reagan et al., *Endocrinology* 109, 1663–1671 (1981).
Li et al., *J. Biol. Chem.* 218, 41–52 (1956).
Lewis et al., *Biochim. Biophys. Res. Comm.* 67, 617–624 (1975).
Mills et al., *Biochim. Biophys. Acta* 742, 169–174 (1983).
Li, C. H., *J. Gen. Physiol.* 45, 169–178 (1962).
Lewis et al., *Endocrinology* 101, 1587–1603 (1977).
Gertler et al., *Endocrinology* 118, 720–726 (1986).
Ashkenazi et al., *Endocrinology* 121, 414–419 (1987).
Graf et al., *Biochem* 13, 5408–5415 (1974).
Maciag et al., *J. Biol. Chem.* 255, 6064–6070 (1980).

Primary Examiner—F. T. Moezie
Attorney, Agent, or Firm—Joseph A. Jones; Leroy Whitaker; William C. Martens

[57] ABSTRACT

This specification describes modified growth hormone having substantially diminished insulin-like and diabetogenic potencies relative to the native hormone with retention of substantially all of the anabolic potency of the native hormone. The modified growth hormone has the following structure: (a) elimination of from 1–5 to 1–19 amino acid residues from the amino terminus of the hormone; (b) cleavage of a peptide bond at any point from the carboxy moiety of residue 127 to residue 153; and (c) optionally, elimination of one or more of amino acid residues 128–152 of the hormone.

10 Claims, No Drawings

PROTEINS HAVING GROWTH HORMONE ANABOLIC PROPERTIES WITH REDUCED EFFECT ON CARBOHYDRATE METABOLISM

BACKGROUND OF THE INVENTION

Human growth hormone (hGH) is a single chain polypeptide hormone containing 191 amino acids and two disulfide bonds. hGH is synthesized by the somatotropic cells of the anterior pituitary and plays an important role in somatic growth through its effects on the metabolism of proteins, carbohydrates, and lipids. At least four distinct biological activities have been ascribed to the mammalian growth hormone molecule, viz., (1) growth promotion, (2) lactogenic activity, (3) diabetogenic activity, and (4) insulin-like activity. This hormone has been used successfully in replacement therapies to treat pituitary dwarfism. Because of its anabolic properties, hGH is considered to be a candidate for use in the treatment of a variety of other medical conditions. However, its effects on carbohydrate metabolism are viewed as potential limitations in its utility in certain situations. As noted, hGH is reported to possess an early insulin-like activity which, in laboratory animals, causes a drop in serum glucose and a drop in serum free fatty acids. In addition, hGH has a diabetogenic activity which is observed several hours after administration of the hormone to test animals. In response to an oral glucose challenge, both serum glucose and insulin levels are elevated with a concomitant insulin resistant glucose intolerance. Although the data are limited in adult human subjects treated with hGH, the potential exists that the same metabolic perturbations may occur. For this reason, a non-diabetogenic form of hGH that retains its anabolic properties is highly desirable for use in treating adult humans.

We have discovered that the structure of growth hormones can be modified to eliminate or substantially reduce both the insulin-like and diabetogenic effects with retention of all or a portion of the growth hormone anabolic properties. It is to such a class of compounds that this invention is directed.

It has long been a research goal to separate these activities and to isolate a growth hormone "active core" having only or dominantly anabolic activity. Although there are a number of reports in the literature describing various modifications of human growth hormone (hGH), the goal of isolating the growth hormone "active core" has remained unfulfilled.

Three naturally-occurring, proteolytically cleaved, two-chain forms of human growth hormone have been characterized and are designated 24K, $\alpha_2$, and $\alpha_3$. These derivatives are described in a review article by Lewis et al., *Rec. Progr. Horm. Res.* 36, 477-508 (1980). The 24K form, which has been isolated from the pituitary, results from a single cleavage at $Phe_{139}$. The $\alpha_2$ form has been cleaved so as to remove residues 135 through 140, and the $\alpha_3$ form is lacking residues 135 through 146. These derivatives in general show a potentiation of growth stimulating activity as well as an increase in lactogenic activity.

In addition to the naturally occurring derivatives, there is an extensive literature on the use of enzymes to proteolytically modify human growth hormone. Included among enzymes that have been used are trypsin, chymotrypsin, plasmin, thrombin, subtilisin, bromelain, fibrinolysin, and pepsin.

The use of trypsin to modify human growth hormone was first reported in 1965 by Li and Samuelsson, *Mol. Pharmacol.* 1, 47-52 (1965). These authors treated human growth hormone with trypsin for varying lengths of time and then tested the biological activities of the digests. They found that digestion for up to 30 minutes resulted in little loss of growth-promoting activity as measured by the rat tibia assay or little loss of lactogenic activity as measured by the pigeon crop sac assay. Longer digestion times resulted in a gradual loss of growth-promoting activity and an abrupt loss of lactogenic activity. More recently, Graf et al., *J. Biol. Chem.* 257, 2365-2369 (1982), have characterized a product of the trypsinolysis of human growth hormone as a derivative lacking residues 135 through 145. This derivative has similar properties to the intact hormone in two receptor-binding assays, a radioimmunoassay, and the rat tibia assay.

The enzyme plasmin has been extensively used to modify human growth hormone. Mills et al., *Endocrinol.* 102, 1366-1376 (1978), report on the digestion of reduced and S-carbamidomethylated human growth hormone with the isolation of several fractions and derivatives including, (1) the S-carbamidomethylated fragment consisting of residues 1-134, (2) fragment 20-41, (3) fragment 95-134, (4) the carbamidomethylated fragment 1-134 joined in a noncovalent complex with the carbamidomethylated fragment 141-191, (5) the deamidated noncovalent complex of the carbamidomethylated fragment 1-134 and the carbamidomethylated fragment 141-191, (6) a 1:1 deamidated noncovalent complex of carbamidomethylated fragments 1-134, 42-134, and 141-191, (7) Da, a fraction isolated from an anion exchange separation of the plasmin digest, (8) Db, a second, more acidic fraction isolated from the same anion exchange column, and (9) Dc, a third, more acidic fraction isolated from the same anion exchange column. Da and Db are reported to be equipotent with human growth hormone in the rat weight gain assay for growth-promoting activity. In a second paper from the same group, Reagan et al., *Endocrinol.* 102, 1377-1386 (1978), these derivatives are more extensively characterized biologically. Derivatives (4) and (5) were found to retain most of their growth-promoting activity in the rat weight gain assay and to be superpotent in a lactogenic assay. In contrast, derivative (6) had only about ⅓ the growth-promoting activity relative to intact human growth hormone but was equipotent in the lactogenic assay. Fraction (7) retained the growth-promoting activity and insulin-like activity as measured by glucose oxidation in rat epididymal adipose tissue, and exhibited slightly higher lactogenic activity. Fraction (8) retained the growth-promoting activity but lost about ½ of the insulin-like activity. Fraction (9) retained about 44% of the growth-promoting activity but was not tested for other biological activities. The unfractionated plasmin digest was found to have about ½ the growth-promoting activity and ½ the insulin-like activity of intact human growth hormone and about ¾ of the lactogenic activity. The diabetogenic activity of some of these derivatives was tested in obese ob/ob [Reagan, *Diabetes* 27, 883-888 (1978)]. The unfractionated plasmin digest was found to retain 100% of the diabetogenic acitivity of intact human growth hormone, as was the S-carbamidomethylated derivative. Derivatives (4) and (6) likewise were found to be diabetogenic; however, derivative (2) had no diabetogenic activity.

Thrombin cleaves at a single site within the human growth hormone molecule, at $Arg_{134}$, giving rise to a two-chain molecule with the two chains connected by a disulfide bond. Reduction and alkylation of the disulfide bond results in a noncovalent complex of the two chains. Several derivatives of this nature have been isolated from thrombin digests of human growth hormone [Mills et al., *Endocrinol.* 107, 391-399 (1980) and Reagan et al., *Endocrinol.* 109, 1663-1671 (1981)] including, (1) the derivative with the single clip at $Arg_{134}$, (2) the S-carbamidomethylated noncovalent complex, (3) the S-aminoethylated noncovalent complex, (4) the S-carboxymethyl noncovalent complex, (5) the carbamidomethylated fragment 1-134, and (6) the carbamidomethylated fragment 135-191. Biological assays on these derivatives included the rat weight gain assay for growth-promotion, the oxidation of glucose as a measure of insulin-like activity, the obese ob/ob mouse assay for diabetogenic activity, and the N-acetyllactosamine synthase assay for lactogenic activity. Derivative (1) was fully potent in all assays except the diabetogenic assay in which it was not tested. Derivatives (2) and (3) were only 50% potent in the weight gain assay and 20% potent in the insulin-like assay, but were 75-80% potent in the lactogenic assay. Again, these two derivatives were not tested in the diabetogenic assay. Derivative (4) was found to have only 10% of the growth-promoting activity and 5% of the insulin-like activity but was fully potent in the lactogenic assay. Fragments (5) and (6) were found to have only slight activity in the weight gain assay and the insulin-like activity was very low. However, while fragment (5) possessed 25-50% of the diabetogenic activity of intact human growth hormone, fragment (6) had no detectible activity.

Li et al., *J. Biol. Chem.* 218, 41-52 (1956) studied the biological properties of the products of a chymotrypsin digest of human growth hormone. They found that increasing times of incubation resulted in a gradual loss of growth-promoting activity as measured by the rat tibia assay. However, even after 300 minutes of incubation, the digest still retained 75% of the activity of intact human growth hormone. An "active core" was obtained by dialysis of a chymotrypsin digest and was found to retain full potency.

Fibrinolysin has been used to modify human growth hormone by removal of a peptide consisting of residues 138 through 147 [Lewis et al., *Biochem. Biophys. Res. Comm.* 67, 617-624 (1975)]. This derivative was found to have greatly enhanced growth-promoting activity and lactogenic activity.

The digestion of human growth hormone with bromelain results in a mixture of three components, all three with a large fragment consisting of residues 1-134 and a smaller fragment consisting of either residues 143-191, 145-191, or 146-191. This mixture retained 70-80% of the growth-promoting activity of intact human growth hormone and 100% of the insulin-like activity [Mills et al., *Biochim. Biophys. Acta* 742, 169-174 (1983)]. If the above mixture is reduced and S-carbamidomethylated, all three of the alkylated smaller fragments can be isolated. These fragments could then be complemented with S-carbamidomethylated fragment 1-134 obtained from a thrombin digest resulting in a mixture of noncovalent complexes consisting of the alkylated analogs of the three derivatives. These were found to be sustantially less potent in both the growth-promoting and the insulin-like activity assays.

Pepsin was used to digest human growth hormone [Li, *J. Gen. Physiol.* 45, 169-178(1962)]. Growth-promoting activity was found to decrease with increasing periods of digestion, but even after 120 minutes, approximately 66% of the original activity remained. Lactogenic activity was fully retained at 60 minutes of digestion, but further digestion resulted in complete abolition of activity. An "active core" was isolated from the digestion by dialysis and retained 100% of the growth-promoting activity.

Limited hydrolysis of human growth hormone with subtilisin results in the formation of three two chain derivatives, $S_1$, $S_2$, and $S_3$ [Lewis et al., *Endocrinol.* 101, 1587-1603 (1977)]. $S_1$ consists of residues 1-139 connected through a disulfide bond to a fragment consisting of residues 150-191. $S_2$ consists of residues 1-139 connected through a disulfide bond to a fragment consisting of residues 147-191. $S_3$ is a deamidated derivative of $S_2$. These three derivatives were tested in the rat tibia assay and were found to possess excellent growth-promoting activity. They were also tested for diabetogenic activity in dogs using oral glucose tolerance tests. $S_1$ was found to be the most active in producing hyperglycemia and hyperinsulinemia. $S_2$ and $S_3$ were also diabetogenic but less so than $S_1$.

There are two reports in the literature concerning a truncated analog of human growth hormone, prepared by recombinant DNA technology, which lacks the first 13 residues at the amino terminus. [Gertler et al., *Endocrinol.* 118, 720-726 (1986) and Ashkenazi et al., *Endocrinol.* 121, 414-419 (1987)]. This analog was found to inhibit the lactogenic activity of both human growth hormone and ovine prolactin in Nb2 cells and in explants from bovine lactating mammary gland. However, it did not have growth-promoting activity in the Nb2 cells line nor did it affect glucose uptake by the mammary gland explants. It did compete with radiolabeled human growth hormone for binding to Nb2 cells, IM-9 cells, the microsomal fraction from lactating bovine mammary gland, and the the microsomal fraction from rat liver, but with a much lower affinity.

Other growth hormones, primarily bovine, ovine, and rat have been modified proteolytically using many of the same enzymes as used for human growth hormone and their biological properties have been studied. The results are generally the same as those obtained with human growth hormone, i.e., proteolytic modification of the hormones resulted in an alteration of the biological properties. Only two examples will be given here, one using rat growth hormone and proteolysis by trypsin and the other using bovine and ovine growth hormone and proteolysis by trypsin. Maciag et al., *J. Biol. Chem.* 255, 6064-6070 (1980), found that limited trypsin hydrolysis of rat growth hormone resulted in the generation of two fragments, one consisting of residues 1-95 and residues 134-191 linked by a disulfide bond, and the other fragment consisting of residues 96-133. These two derivatives were examined for their abilities to interact with isolated hepatocytes and to stimulate growth in the rat tibia assay. The larger fragment displayed binding properties similiar to those of intact growth hormone but had little or no growth-promoting activity. The smaller fragment interacted weakly with growth hormone receptor sites but possessed significant growth-promoting activity.

Graf and Li, *Biochem.* 13, 5408-5415 (1974) digested both bovine and ovine growth hormones with trypsin and isolated a fragment from each digest that corresponded to residues 96-133 and a fragment from the bovine growth hormone digest that corresponded to residues 151-191. These derivatives were tested in the rat tibia assay for growth-promoting activity and all three were found to have measurable activity.

Thus, many derivatives of human growth hormone have been described resulting in alterations of the biological properties of the molecule. However, none of these derivatives involves both a truncation at the N-terminus as well as a cleavage or deletion in the large loop. Furthermore, none of these derivatives retains substantially all of the anabolic activity while having substantially diminished insulin-like and diabetogenic activities.

SUMMARY OF THE INVENTION

Thus, this invention is directed to a modified growth hormone having substantially diminished insulin-like and diabetogenic potencies relative to the native hormone with retention of substantially all of the anabolic potency of the native hormone.

More particularly, this invention is directed to a modified growth hormone having anabolic properties and substantially reduced insulin-like and diabetogenic effects relative to the corresponding native growth hormone and having a structure differing from that of the growth hormone by a) elimination of a sequence of amino acid residues from the amino terminus of the structure of human growth hormone, such sequence being at least amino acid residues 1-5 but not more than amino acid residues 1-19, or, if a non-human growth hormone, elimination of an equivalent sequence;

b) cleavage of a peptide bond at any point from the carboxyl moiety of residue 127 to the amino moiety of residue 153 of the structure of human growth hormone, or, if a non-human growth hormone, cleavage of a peptide bond at an equivalent residue; and c) optionally, elimination of one or more of amino acid residues 128-152 of the structure of human growth hormone, or, if a non-human growth hormone, elimination of one or more equivalent amino acid residues.

DETAILED DESCRIPTION OF THE INVENTION

As noted, this invention relates to the finding that the growth hormone molecule can be modified structurally to substantially reduce its insulin-like and diabetogenic effects with retention of anabolic activity.

By the term "substantially diminished" or any recognized variants of the term as used herein is meant loss of at least about 60% of the native hormone insulin-like and diabetogenic potencies. By the term "substantially all" or any recognized variants of the term is meant retention of greater than about 60% of the native hormone anabolic potency.

Preferred compounds of this invention are those having at least about 70% of the native hormone anabolic potency with loss of at least about 90% of both the native hormone insulin-like and diabetogenic potencies.

The term "modified", when used herein in conjunction with growth hormone is intended merely to describe the structure of molecule and not its source. That is, a "modified growth hormone", as that term is used herein, is not limited to molecules produced from intact growth hormone. The "modified growth hormone", however prepared, will be within the scope of the compounds contemplated as within this invention so long as its structure is associated with and based upon that of the growth hormone with which it is related.

In particular and preferably, when the modified growth hormone is structurally related to human growth hormone, the structure of the modified human growth hormone will be such that, relative to native human growth hormone, it will have a sequence of amino acid residues at the amino terminus removed. The removed sequence represents at least the first five amino acid residues (Phe-Pro-Thr-Ile-Pro) but not greater than the first 19 amino acid residues 10
(Phe—Pro—Thr—Ile—Pro—Leu—Ser—Arg—Leu—Phe—
—Asp—Asn—Ala—Met—Leu—Arg—Ala—His—Arg)

of human growth hormone.

Although the portion removed from the amino terminus may range anywhere from residues 1-5 to residues 1-19, preferably, the excised sequence ranges from residues 1-7 to residues 1-12. Most preferably, residues 1-8 are removed.

In addition, the modified human growth hormone differs from the native hormone in that the peptide chain has been cleaved at any point extending from the carboxyl moiety of residue 127 (Arg) to the amino moiety of residue 153 (Asp).

Optionally, the modified human growth hormone may be further altered by elimination of all or any portion of the sequence represented by residues 128-152 of human growth hormone. This sequence is as follows:

130
—Leu—Glu—Asp—Gly—Ser—Pro—Arg—Thr—Gly—

140
—Gln—Ile—Phe—Lys—Gln—Thr—Tyr—Ser—Lys—Phe—

150
—Asp—Thr—Asn—Ser—His—Asn—

Preferably, the structure of the modified human growth hormone is such that residues 135-145 have been eliminated.

When the modified growth hormone of this invention is based upon a non-human growth hormone, the foregoing criteria apply, the only exception being that the sequences which have been removed or modified are those analogous to those defined above for human growth hormone.

Thus, for example, applying the above to the sequences depicted in Abdel-Mequil et al., *Proc. Natl. Acad. Sci. U.S.A.* 84, 6434-6437 (1987), at page 6437, leads to the following modifications relative to the corresponding native growth hormone:

| Growth Hormone | Range of Residues Removed, Amino Terminus | Range of Residues Optionally Removed, Mid-chain |
| --- | --- | --- |
| porcine | 1-6 to 1-20 | 127-151 |
| bovine | 1-6 to 1-20 | 127-151 |
| ovine | 1-6 to 1-20 | 127-151 |
| horse | 1-5 to 1-19 | 126-150 |
| avain | 1-6 to 1-20 | 127-151 |

For convenience, compounds of this invention are named based upon the native hormone and those portions thereof that have been removed and/or the point of internal chain cleavage. Thus, examples of compounds of this invention are:

Des$_{1-5,128-152}$-human growth hormone;
Des$_{1-8,130-138}$-bovine growth hormone:
Des$_{1-15,132-145}$-porcine growth hormone;
Des$_{1-10}$, Split$_{132-133}$-human growth hormone;
Des$_{1-8,135-145}$-human growth hormone;
Des$_{1-14,140-145}$-ovine growth hormone;
Des$_{1-12,126-140}$-horse growth hormone;
Des$_{1-19,130-133}$-avian growth hormone;
Des$_{1-9,135-138}$-human growth hormone;
Des$_{1-13}$, Split$_{150-151}$-human growth hormone;
Des$_{1-16,129-132}$-human growth hormone:
Des$_{1-11}$, Split$_{143-144}$-human growth hormone;

and the like. The compounds of this invention can be prepared using now routine recombinant DNA methodology. Thus, the intended compound can be expressed as a straight chain molecule containing a selective cleavage site at the point at which ultimate internal cleavage is intended. The expression product is first folded using recognized methodology to obtain formation of the two disulfide bonds such as are present in human growth hormone by reaction of cysteine residues at positions 53 and 165 and positions 182 and 189, respectively.

Following the folding reaction, the resulting product can be cleaved by known methods using trypsin and carboxypeptidase B. This cleavage is achieved by tailoring the expression molecule to incorporate at the cleavage site a dibasic dipeptide sequence, such as -Lys-Arg- or -Arg-Arg-. Upon treatment with trypsin and carboxypeptidase B, the desired molecule is formed with accompanying loss of the dibasic dipeptide.

Also contemplated within the scope of this invention are compounds as aforedescribed containing a methionine residue at the amino terminus. The presence of the methionine residue arises in those instances in which the product has been produced by recombinant DNA methodology, and the resulting single straight chain intermediate protein expression product contains an initiating methionine residue. Although the methionine can be removed by recognized methodology, whether by direct cleavage of the methionine or by expression of a protein having a cleavage site which facilitates methionine removal, compounds retaining initiating methionine are regarded as part of this invention.

Certain of the compounds of this invention can also be prepared by enzymatic treatment of the native hormone. Thus, for example, controlled trypsinolysis of human growth hormone permits production of Des$_{1-8,135-145}$-human growth hormone, one of the preferred compounds of this invention.

As noted, the compounds of this invention have an anabolic effect comparable to that of a growth hormone but with substantially diminished insulin-like and/or diabetogenic effects present in growth hormones.

The compounds of this invention, due to their anabolic activity, are useful in the post-surgical (trauma) healing process; Turner's syndrome; Total Parenteral Nutrition (TPN); growth in short normal stature children (not necessarily dwarfism); malnutrition start up; osteoporosis (longterm treatment); wound healing, including stasis ulcers, decubitus ulcers, and diabetic ulcers; old age cachectic states (general anabolism); and chronic renal failure. As such they can be used in a variety of pharmaceutical compositions and formulations and can be administered by a variety of conventional routes, such as intramuscular, intravenous, subcutaneous, and intraperitoneal.

In administering the compounds of this invention, the pharmaceutical forms suitable for injection include sterile aqueous solutions or dispersions and sterile powders for reconstitution into sterile injectable solutions or dispersions.

Sterile injectable solutions can be prepared by incorporating the compounds of this invention in the desired amount of an appropriate recognized solvent along with, as desired, various other routine ingredients used in pharmaceutical formulations.

The following example is provided to illustrate this invention. It is not intended to be limiting on the scope thereof.

EXAMPLE

Preparation of Des$_{1-8,135-145}$-Human Growth Hormone (Des$_{1-8,135-145}$-hGH).

A. Conversion of Human Growth Hormone

Des$_{1-8,135-145}$-hGH was prepared by the action of trypsin on biosynthetic human growth hormone (hGH). Approximately 1 gram of hGH was dissolved at a concentration of 10 mg/ml in a buffer of 50 mM Tris-acetate pH 7.5, and 20 mg of trypsin (TPCK) (Cooper Biomedical) was added giving a weight ratio of trypsin to hGH of 1/50. This reaction mixture was incubated at 37° C. for approximately 1 hour at which point the reaction was terminated by the addition of 5 mg of the trypsin inhibitor, N-tosyl-L-lysine chloromethyl ketone (TLCK). The reaction mixture was clarified by filtration through a Millipore filter (0.45 um), and the desired product was isolated and purified by the following chromatographic procedures.

B. Q-Sepharose Fast Flow

A column (2.2×28 cm) was packed with approximately 100 ml of Q-Sepharose Fast Flow (Pharmacia) and was equilibrated in buffer A (50 mM Tris-HCl pH 8, 30% acetonitrile, 0.10M NaCl). The clarified reaction mixture from the preceeding step was applied and protein was eluted with a linear salt gradient generated by mixing buffer A and buffer B (50 mM tris-HCl pH 8, 30% acetonitrile, 0.14M NaCl). The gradient was 0–100% B over 960 minutes at a flow rate of approximately 26 ml/cm$^2$/hr. Elution of protein was monitored spectrophotometrically at 280 nm. Fractions containing the desired product were localized by analyzing with the Mono Q assay described below.

C. Reversed-phase HPLC

A reversed-phase HPLC column (1×15 cm) and packed with 10 micron, C-8 silica (Dupont) was equilibrated in a solvent consisting of 50 mM Tris-HCl pH 8, 16.5% acetonitrile, 22.5% n-propanol. The pooled fractions from the Q-Sepharose Fast Flow column were applied, and protein was eluted with a gradient generated by mixing Solvent A (50 mM Tris-HCl pH 8, 30% acetonitrile) and Solvent B (50 mM Tris-HCl pH 8, 50% n-propanol). The gradient was 45–65% B over 160 minutes at a flow rate of 0.25 ml/min. Elution was monitored spectrophotometrically at 220 nm. Fractions containing the desired product were localized using the Mono Q assay described below.

D. Sephadex G25

The fractions from the reversed-phase column containing the desired product were pooled and applied to a column (2.2×26 cm) packed with Sephadex G-25 to remove organic solvents and buffer salts. The column was equilibrated using ammonia-buffered water at pH 8, the pooled fractions were applied, and the protein was eluted using the same solvent at a flow rate of 3 ml/min. Elution of the protein was monitored spectrophotometrically at 280 nm, and those fractions containing significant absorbance were pooled and lyophilized to obtain 12.9 mg of $Des_{1-8,135-145}hGH$.

E. Assay for $Des_{1-8,135-145}hGH$.

The assay used to monitor product formation and to measure $Des_{1-8,135-145}hGH$ in column fractions was a chromatographic assay utilizing a Mono Q HR 5/5 column (Pharmacia). The buffers employed were A: 50 mM Tris-HCl pH 8, 30% acetonitrile and B: 50 mM Tris-HCl pH 8, 30% acetonitrile, 0.2M NaCl. The flow rate was 1.0 ml/min and the gradient was 0-100% B over 20 minutes. The elution of protein from the column was followed spectrophotometrically at either 214 nm or 280 nm.

Biological Activity of $Des_{1-8,135-145}hGH$

The anabolic actions of growth hormone (GH) are expressed in retention of nitrogen, water, and minerals and in the synthesis of total body DNA, RNA, and protein. Growth hormone also has two contrary effects: (a) an early insulin-like effect, and (b) a later diabetogenic effect. The insulin-like effects of GH are most easily demonstrated in the laboratory using fasted (overnight) hypophysectomized rats. When human growth hormone (hGH) is administered to fasted hypophysectomized rats, it causes transient decreases in serum glucose and free fatty acid (FFA) concentrations. Transient decreases in serum glucose and FFA concentrations were not induced in fasted hypophysectomized rats one hour following intraperitoneal injection of $Des_{1-8,135-145}hGH$.

The results of the experiment are shown in Table 1.

TABLE 1

The Effect of hGH and $Des_{1-8,135-145}hGH$ on Serum Glucose and Free Fatty Acid Concentrations of Fasted Female Hypophysectomized Rats

| Experimental[a] Groups | Serum Glucose (mg/dl) | Serum FFA (uEq/ml) |
|---|---|---|
| Control | 79.5 ± 3.3[b] | 0.645 ± 0.031 |
| hGH (25 ug) | 80.6 ± 2.5 | 0.737 ± 0.029 |
| hGH (50 ug) | 59.6 ± 3.4* | 0.366 ± 0.035* |
| hGH (100 ug) | 47.5 ± 3.9* | 0.462 ± 0.070* |
| hGH (200 ug) | 32.4 ± 2.6* | 0.202 ± 0.012* |
| $Des_{1-8,135-145}hGH$ (25 ug) | 85.2 ± 2.1 | 0.747 ± 0.025 |
| $Des_{1-8,135-145}hGH$ (50 ug) | 76.6 ± 5.3 | 0.604 ± 0.061 |
| $Des_{1-8,135-145}hGH$ (100 ug) | 88.9 ± 5.8 | 0.654 ± 0.052 |
| $Des_{1-8,135-145}hGH$ (200 ug) | 79.6 ± 4.3 | 0.710 ± 0.063 |

[a] n = 6 rats/group
[b] Mean ± SEM
*p ≤ 0.05; significant differences determined using a two-tailed Dunnett's test.

Confirmation of the early insulin-like effects of growth hormone has been demonstrated in vitro using male rat epididymal adipose tissue. Normal growth hormone, like insulin, has been shown to stimulate the uptake of glucose into epididymal adipose tissue in vitro and cause the glucose to be converted to carbon dioxide ($CO_2$) and lipid. Table 2 shows that while various doses of hGH caused the conversion of glucose to $CO_2$, $Des_{1-8,135-145}hGH$ had no effect on that conversion. Table 2 also shows that while various doses of hGH caused the conversion of glucose to lipid, no dose of $Des_{1-8,135-145}hGH$ causes that same conversion. These results in vitro confirm the lack of effects in vivo and suggest that $Des_{1-8,135-145}hGH$ has no early insulin-like activity.

TABLE 2

The Effect of $Des_{1-8,135-145}hGH$ and Human Growth Hormone Oxidation of Glucose to Carbon Dioxide by Epididymal Fat Pad Tissue In Vitro

| Experimental Compound | Dose (μg/ml) | Δ μM Glucose C/ mgm M/3HR |
|---|---|---|
| A. Glucose Conversion to Carbon Dioxide | | |
| Human Growth Hormone | 0 | 0.0 ± 0.0 |
| | 50 | 0.1 ± 0.4[a] |
| | 100 | 1.5 ± 0.2* |
| | 200 | 2.5 ± 0.4* |
| $Des_{1-8,135-145}hGH$ | 0 | 0.0 ± 0.0 |
| | 50 | 0.4 ± 0.2 |
| | 100 | 0.5 ± 0.5 |
| | 200 | 0.5 ± 0.5 |
| B. Glucose Conversion to Lipid | | |
| Human Growth Hormone | 0 | 0.0 ± 0.0 |
| | 50 | 0.2 ± 0.1 |
| | 100 | 1.8 ± 0.5* |
| | 200 | 5.5 ± 1.5* |
| $Des_{1-8,135-145}hGH$ | 0 | 0.0 ± 0.0 |
| | 50 | 0.3 ± 0.3 |
| | 100 | 0.0 ± 1.0 |
| | 200 | 0.0 ± 1.0 |

[a] Mean ± SEM
*Statistical significance of means determined by Dunnett's Test

Contrary to its early insulin-like activity, hGH also has a diabetogenic or anti insulin-like activity. This activity occurs several hours after a single injection of hGH. Multiple injections of hGH over a long period of time can lead to temporary or permanent diabetes (insulin resistant glucose intolerance). Administration of $Des_{1-8,135-145}hGH$ under the same conditions had no effect on baseline serum insulin or glucose concentrations in adult female beagle dogs. In addition, $Des_{1-8,135-145}hGH$ had no effect on the serum glucose or insulin concentrations in response to an oral glucose challenge.

Two experimental procedures were used to demonstrate the lack of diabetogenicity of $Des_{1-8,135-145}hGH$: (a) the acute, and (b) the chronic administration of $Des_{1-8,135-145}hGH$ to adult female beagle dogs. In the first experiment, the dogs were given an oral glucose tolerance test (OGTT) before and 12 hours after a single subcutaneous injection of $Des_{1-8,135-145}hGH$ (0.125, 0.250, or 0.50 mg/kg). None of the doses of $Des_{1-8,135-145}hGH$ had an effect on baseline serum insulin or glucose concentrations, and none of the doses had an effect on serum glucose or insulin levels in response to a glucose challenge. In the second experiment, the dogs were given a short course (7 injections over a 7 day period) of treatment with $Des_{1-8,135-145}hGH$ (0.250 and 0.500 mg/kg) by subcutaneous injection. Oral glucose tolerance tests were administered before the treatment started and 12 hours after the last injection of $Des_{1-8,135-145}hGH$. Neither dose of $Des_{1-8,135-145}hGH$ had an effect on baseline serum glucose or insulin concentrations or serum glucose or insulin in response to the oral glucose challenge. The results of these experiments demonstrate that $Des_{1-8,135-145}hGH$ has no diabetogenic activity in dogs at the doses used.

The growth promoting activity of Des$_{1-8,135-145}$hGH was determined in a 10 day bioassay using hypophysectomized rats and measuring increased body weight gain and increased proximal tibial cartilage width. In all bioassays conducted, Des$_{1-8,135-145}$hGH demonstrated approximately 70 percent the biological activity of native hGH. In addition to the bioassay, Des$_{1-8,135-145}$hGH has been shown to cause a reduction in both urinary and serum urea nitrogen concentrations. This anabolic effect demonstrates that Des$_{1-8,135-145}$hGH causes the retention of nitrogen for use in protein biosynthesis.

We claim:

1. A modified growth hormone having substantially diminished insulin-like and diabetogenic potencies relative to the native hormone with retention of substantially all of the anabolic potency of the native hormone, in which the structure differs from that of the corresponding native growth hormone by
   a) elimination of a sequence of amino acid residues from the amino terminus of the structure of human growth hormone, such sequence being at least amino acid residues 1-5 but not more than amino acid residues 1-19, or, if a non-human growth hormone, elimination of an equivalent sequence;
   b) cleavage of a peptide bond at any point from the carboxyl moiety of residue 127 to the amino moiety of residue 153 of the structure of human growth hormone, or, if a non-human growth hormone, cleavage of a peptide bond at an equivalent residue; and
   c) optionally, elimination of one or more of amino acid residues 128-152 of the structure of human growth hormone, or, if a non-human growth hormone, elimination of one or more equivalent amino acid residues.

2. Modified growth hormone of claim 1, in which the corresponding native growth hormone is human growth hormone.

3. Modified growth hormone of claim 2, in which the amino acid residues eliminated from the amino terminus are at least amino acid residues 1-7 but not more than amino acid residues 1-12.

4. Modified growth hormone of claim 3, in which the amino acid residues eliminated from the amino terminus are amino acid residues 1-8.

5. Modified growth hormone of claim 2, in which a peptide bond at any point from the carboxyl moiety of residue 127 to the amino moiety of residue 153 is cleaved without elimination of any of amino acid residues 128-152.

6. Modified growth hormone of claim 2, in which a peptide bond at any point from the carboxyl moiety of residue 127 to the amino moiety of residue 153 is cleaved with elimination of one or more of amino acid residues 128-152.

7. Modified growth hormone of claim 6, in which residues 135-145 have been eliminated.

8. Modified growth hormone of claim 7, in which the amino acid residues eliminated from the amino terminus are at least amino acid residues 1-7 but not more than amino acid residues 1-12.

9. Modified growth hormone of claim 8, in which the amino acid residues eliminated from the amino terminus are amino acid residues 1-8.

10. Modified growth hormone of claim 1, in which the amino terminus is further modified to contain an initiating methionine residue.

* * * * *